(12) United States Patent
Midori Laga et al.

(10) Patent No.: US 12,383,483 B2
(45) Date of Patent: Aug. 12, 2025

(54) COMPOSITIONS AND METHODS FOR STYLING THE HAIR

(71) Applicant: L'Oreal, Paris (FR)

(72) Inventors: Stephanie Midori Laga, Rahway, NJ (US); Seyma Aslan, Clifton, NJ (US)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 17/219,800

(22) Filed: Mar. 31, 2021

(65) Prior Publication Data

US 2022/0313583 A1 Oct. 6, 2022

(51) Int. Cl.
| | |
|---|---|
| A61K 8/60 | (2006.01) |
| A61K 8/06 | (2006.01) |
| A61K 8/31 | (2006.01) |
| A61K 8/34 | (2006.01) |
| A61K 8/37 | (2006.01) |
| A61K 8/41 | (2006.01) |
| A61K 8/42 | (2006.01) |
| A61K 8/73 | (2006.01) |
| A61K 8/92 | (2006.01) |
| A61Q 5/06 | (2006.01) |

(52) U.S. Cl.
CPC ............... *A61K 8/60* (2013.01); *A61K 8/06* (2013.01); *A61K 8/31* (2013.01); *A61K 8/342* (2013.01); *A61K 8/345* (2013.01); *A61K 8/37* (2013.01); *A61K 8/416* (2013.01); *A61K 8/42* (2013.01); *A61K 8/732* (2013.01); *A61K 8/922* (2013.01); *A61Q 5/06* (2013.01); *A61K 2800/48* (2013.01); *A61K 2800/5422* (2013.01); *A61K 2800/88* (2013.01)

(58) Field of Classification Search
CPC ........... A61K 8/60; A61K 8/345; A61K 8/416
See application file for complete search history.

(56) References Cited

U.S. PATENT DOCUMENTS

| | | |
|---|---|---|
| 3,951,156 A | 4/1976 | Gadzala et al. |
| 4,137,180 A | 1/1979 | Naik et al. |
| 4,874,554 A | 10/1989 | Lang et al. |
| 7,635,465 B2 | 12/2009 | Makino |
| 7,942,937 B2 | 5/2011 | Brun |
| 10,617,613 B2 | 4/2020 | Parikh et al. |
| 10,813,868 B2 | 10/2020 | Khoshdel et al. |
| 12,156,930 B2 | 12/2024 | Parikh et al. |
| 2002/0013481 A1 | 1/2002 | Schonrock et al. |
| 2005/0226838 A1 | 10/2005 | Krause et al. |
| 2011/0311655 A1 | 12/2011 | Ross |
| 2012/0080045 A1* | 4/2012 | Hata ............... A61Q 5/12 132/202 |
| 2013/0330373 A1 | 12/2013 | Lee |
| 2018/0353401 A1 | 12/2018 | Wossene et al. |
| 2020/0163867 A1 | 5/2020 | Viscoglios et al. |
| 2020/0206111 A1* | 7/2020 | Lee ............... A61Q 5/12 |
| 2021/0059922 A1 | 3/2021 | Ghani et al. |
| 2021/0093543 A1 | 4/2021 | Parikh et al. |
| 2021/0212918 A1* | 7/2021 | Uzan ............... C08L 35/02 |

FOREIGN PATENT DOCUMENTS

| | | |
|---|---|---|
| CN | 101455622 A | 6/2009 |
| CN | 108309925 A | 7/2018 |
| EP | 3527264 A1 | 8/2019 |
| KR | 10-2009-0078095 | 7/2009 |
| KR | 10-2012-0049122 A | 5/2012 |
| WO | 2007079793 A1 | 7/2007 |
| WO | 2012/095410 A1 | 7/2012 |
| WO | 2016/074969 A1 | 5/2016 |
| WO | WO-2020002524 A1 * | 1/2020 ............... A61K 8/60 |
| WO | 2020/122221 A1 | 6/2020 |

OTHER PUBLICATIONS

Keranique, Volumizing Keratin Conditioner, https://web.archive.org/web/20170709070132/https://keranique.com/product_card/Conditioner; accessed Oct. 17, 2022; archived via WayBack Machine Jul. 9, 2017 (Year: 2017).*

Williams et al., Chemistry and Technology of the Cosmetics and Toiletries Industry, 1992, Kluwer Academic Publishers, 1, 26-28; 54-93 (Year: 1992).*

Drummond et al., Sugar Fatty Acid Esters, 2003, CRC Press, 2, 94-128 (Year: 2003).*

Polat et al., Syntheses and Application of Sucrose-Based Ester, 2001, Journal of Surfactants and Detergents, 4, 415-421 (Year: 2001).*

Lukic et al., An Overview of Novel Surfactants for Formulation of Cosmetics with Certain Emphasis on Acidic Active Substances, Tenside Surfactants Detergents, 53(1), 7-19 (Year: 2016).*

2017 Cosmetic Ingredient Review Expert Panel "Amended Safety Assessment of *Mentha piperita* (Peppermint)-derived Ingredients as Used in Cosmetics" (https://www.cir-safety.org/sites/default/files/pepper092017rep_final.pdf; accessed Nov. 9, 2022; published Sep. 22, 2017) (Year: 2017).*

Perkins (NaturallyCurly, Apr. 14, 2015, Want to Stretch or Elongate? These will help? https://www.naturallycurly.com/curlreading/home/want-to-stretch-or-elongate-these-will-help) (Year: 2015).*

(Continued)

*Primary Examiner* — Mark V Stevens

(74) *Attorney, Agent, or Firm* — THE MARBURY LAW GROUP, PLLC

(57) ABSTRACT

The disclosure relates to compositions comprising (a) at least one sucrose ester; (b) at least one nonionic polysaccharide thickening agent; (c) at least one cationic surfactant; (d) at least one emulsifier chosen from fatty alcohols, esters, or a combination thereof; (e) optionally, at least one $C_3$-$C_8$ polyol chosen from diols and triols; and (f) optionally, at least one fatty compound. The compositions can be used as leave-in compositions for styling the hair. The disclosure also relates to kits comprising the compositions and methods of using the compositions.

20 Claims, 2 Drawing Sheets

(56) References Cited

OTHER PUBLICATIONS

French Search Report and Written Opinion for counterpart French Application No. 2107719, dated Mar. 29, 2022.
Mintel: "Restorative Blowout Perfector," Ojon, XP-002744127, Record ID 2038931, Apr. 2013.
Mintel: "Clean Up Peppermint Conditioner," TIGI International, XP-055906356, Record ID 910364, May 8, 2008.
Mintel: "Conditioner," Unilever, XP-055522806, Record ID 675306, Mar. 22, 2007.
Mintel: "Conditioner," Po Care, XP-055906346, Record ID 2760327, Nov. 3, 2014.
Mintel: "Curl Taming Lotion," L'Oreal, XP055906340, Record ID 8131733, Sep. 23, 2020.
French Search Report and Written Opinion for counterpart Application No. FR 2107989, dated Jun. 22, 2022.
Mintel: "Conditioner," Acro, Record ID 6583323, XP055932989, dated May 28, 2019.
Copending U.S. Appl. No. 17/219,811, entitled: Compositions and Methods for Styling the Hair, Inventors: Stephanie Midori Laga et al., filed Mar. 31, 2021.
Copending U.S. Appl. No. 17/219,825, entitled: Compositions and Methods for Styling the Hair, Inventors: Stephanie Midori Laga et al., filed Mar. 31, 2021.
French Search Report and Written Opinion for counterpart Application No. F2107846, dated Jul. 14, 2022.
Mintel: "Curly Hair Shampoo," Panzeri Diffusion/Z.one Concept, Record ID 6380273, XP055942024, Mar. 5, 2019.
Mintel: "Cream Soda Smoothing Cream," Drybar Products, Record ID 2038767, XP002762783, May 1, 2013.
Translation of First Chinese Office Action for counterpart Application No. 201980069978.4, dated Oct. 8, 2022.
Non-Final Office Action for copending U.S. Appl. No. 17/219,825, dated Nov. 22, 2022.
IMGT, "Amino Acids," https://www.imgt.org/IMGTeducation/Aide-memoire/_UK/aminoacids/abbreviation.html; accessed Nov. 3, 2022; archived via Wayback Machine Jul. 5, 2017.
Oshimura et al., "Hair and amino acids: The interactions and the effects," J. Cosmet. Sci., 58, 2007, pp. 347-357.
INCI Beauty, "Glucosamine HCL," https://Incibeauty.com/en/ingredients/501-glucosamine-hcl; accessed Nov. 14, 2022.
Non-Final Office Action for copending U.S. Appl. No. 17/219,811, dated Dec. 22, 2022.
Nihon Emulsion Co., Ltd. Product information Emalex HC-60 https://www.nihon-emulsion.co.jp/products/detail/EMALEX HC-60?lang = en 1/1/ Emalex HC-60 Chemical Composition, Dec. 16, 2022.
BIS-Diglyceryl Polyacyladipate-2, https://www.surfactant.top/en/saa/?type=detail&id=2370, Oct. 20, 2014, 3 pages.
Final Office Action for copending U.S. Appl. No. 17/219,825, dated Jul. 3, 2023.
Haden, "Rinse out or Leave in: Conditioners Decoded," (https://curlsunderstood.com/rinse-out-or-leave-in-conditioners/; accessed Jun. 23, 2023; archived via WayBack Machine Jul. 6, 2017) (Year: 2017).
Final Office Action for copending U.S. Appl. No. 17/219,811, dated Aug. 3, 2023.
Non-Final Office Action in U.S. Appl. No. 17/219,811, mailed Dec. 22, 2023, 17 pages.
Final Office Action in U.S. Appl. No. 17/219,811, mailed Jun. 27, 2024, 20 pages.
Non-Final Office Action in U.S. Appl. No. 17/219,825, mailed Mar. 28, 2024, 14 pages.
Final Office Action for copending U.S. Appl. No. 17/219,825, dated Oct. 31, 2024.
Non-Final Office Action for co-pending U.S. Appl. No. 17/219,811, dated Mar. 25, 2025.
Office Action in U.S. Appl. No. 17/219,825, mailed Jun. 16, 2025, 15 pages.

* cited by examiner

COMPOSITIONS AND METHODS FOR STYLING THE HAIR

TECHNICAL FIELD

The present disclosure relates to compositions and methods for styling the hair. The compositions improve the elongation of hair curls while simultaneously delivering benefits such as curl definition, curl hold, softness, smoothness, and/or frizz control to the hair. The disclosure also relates to kits comprising the compositions and methods of using the compositions.

BACKGROUND

Curly hair usually appears shorter than its actual length. In the multicultural beauty market, there is a desire for products that can elongate hair curls and give more visual length to hair. In addition, reducing the curls of very curly hair may increase the manageability and ease of styling of such hair.

Traditional curl-elongation products generally include heavy galenics or oils, which usually leave a greasy or oily feeling. Products that provide hold, such as styling gels, can also give elongating effects, but these products typically flake on hair. Therefore, the use of these elongation products generally requires frequent hair washing, which may be undesirable for consumers who have high curl patterns and prefer limited number of washdays per week. In addition, traditional elongation of hair, including relaxing or straightening hair, usually involves chemical treatment that may cause damage to the hair fibers and/or irritate the scalp.

As such, consumers desire new and improved styling compositions that can deliver visible elongation to hair curls, and at the same time impart various additional advantageous properties to the hair such as good curl definition, curl hold, hair moisture, softness, smoothness, good bounce, good shine, and/or frizz control.

It has now surprisingly been found that compositions comprising at least one sucrose ester are able to improve the elongation of hair curls, and in the meantime, provide curl definition and curl hold, as well as other benefits such as hair moisture, softness, and/or frizz control to the hair.

SUMMARY

The present disclosure relates to compositions for styling the hair, which may provide beneficial effects, such a curl elongation, to the hair. The compositions are optionally leave-in hair styling compositions. The compositions may comprise (a) at least one sucrose ester; (b) at least one nonionic polysaccharide thickening agent; (c) at least one cationic surfactant; and (d) at least one emulsifier chosen from fatty alcohols, esters, or combinations thereof. Optionally, the compositions may further comprise (e) at least one $C_3$-$C_8$ polyol chosen from diols and triols and/or (f) at least one fatty compound, for example vegetable oil.

The at least one sucrose ester may be chosen from sucrose monoesters, sucrose diesters, sucrose trimesters triesters, and sucrose polyesters, such as sucrose stearate, sucrose distearate, sucrose tristearate, sucrose polystearate, sucrose cocoate, sucrose laurate, sucrose palmitate, sucrose dipalmitate, or mixtures thereof. The at least one sucrose ester may be present in the compositions in an amount of at least 4% by weight, relative to the total weight of the composition, such as about 4% to about 30%, about 5% to about 15%, or about 6% to about 9%.

The at least one nonionic polysaccharide thickening agent may optionally be chosen from gums, celluloses, starches, or mixtures thereof, and may be present in an amount ranging from about 0.01% to about 10% by weight, relative to the total weight of the composition, such as about 0.1% A to about 5%, or about 0.5% to about 2.5%.

The at least one cationic surfactant may be chosen from amidoamine compounds, or from monoalkyl quaternary amines, dialkyl quaternary amines, polyquaternium compounds, salts thereof, or mixtures thereof. The at least one cationic surfactant may be present in an amount ranging from about 0.1% to about 15% by weight, relative to the total weight of the composition, such as about 0.5% to about 10%, or about 1% to about 5%.

The at least one emulsifier may be chosen from alkoxylated or non-alkoxylated, saturated or unsaturated, and linear or branched fatty alcohols, may be liquid or solid fatty alcohols, and may optionally be hydrogenated. The at least one emulsifier may be chosen from glyceryl esters, for example esters of an oligomeric glycerol, arachidyl propionate, phytosterol esters, triglycerides of fatty acids and derivatives thereof, noncrosslinked polyesters resulting from the poly condensation between a linear or branched C4-C50 dicarboxylic acid or polycarboxylic acid and a C2-C50 diol or polyol, aliphatic esters of an ester resulting from the esterification of an aliphatic hydroxycarboxylic acid ester with an aliphatic carboxylic acid, or mixtures thereof. The at least one emulsifier may be chosen from non-glyceryl esters, for example isopropyl esters, cetyl esters, or fatty esters. Mixtures of any of the above may also be chosen. The at least one emulsifier may be present in an amount ranging from about 0.01% to about 15% by weight, relative to the total weight of the composition, such as about 0.1% to about 5%, or about 0.5% to about 3%.

If present, the at least one $C_3$-$C_8$ polyol chosen from diols and triols may, for example, be chosen from ethylene glycol, propylene glycol, butylene glycol, hexylene glycol, pentylene glycol, diethylene glycol, dipropylene glycol, 1,3-propanediol, glycerin, diglycerin, caprylyl glycol, polyethylene glycols, or mixtures thereof, and may be present in an amount of at least about 3% by weight, relative to the weight of the composition, such as from about 3% to about 8%, or from about 4% to about 7%.

If present, the at least one fatty compound may be chosen from vegetable oils, hydrocarbon-based oils of mineral or synthetic origin, fatty acids and esters thereof, waxes, triglycerides, lanolins, alkanes, petrolatum, paraffins, fatty alcohols other than those described above, derivatives thereof, or mixtures thereof, and may be present in an amount ranging from about 0.01% to about 15% by weight, relative to the weight of the composition, such as from about 1% to about 10%, or from about 2% to about 7%.

In one exemplary and non-limiting embodiment, the compositions comprise (a) from about 4% to about 25%, by weight, of at least one sucrose ester; (b) from about 0.01% to about 5% of at least one nonionic polysaccharide thickening agent; (c) from about 0.1% to about 10%, by weight, of at least one cationic surfactant; (d) from about 0.5% to about 10%, by weight, of at least one emulsifier chosen from fatty alcohols, esters, or combinations thereof; (e) optionally, from about 3% to about 15%, by weight, of at least one $C_3$-$C_8$ polyol chosen from diols and triols; and (f) optionally, from about 1% to about 10%, by weight, of at least one fatty compound.

In another exemplary and non-limiting embodiment, the compositions comprise (a) at least one sucrose ester chosen from sucrose stearate, sucrose distearate, sucrose tristearate, sucrose polystearate, sucrose cocoate, sucrose laurate, sucrose palmitate, sucrose dipalmitate, or combinations thereof; (b) at least one nonionic polysaccharide thickening agent chosen from gums, celluloses, starches, or combinations thereof; (c) at least one cationic surfactant chosen from amidoamines, monoalkyl quaternary amines, dialkyl quaternary amines, polyquaternium compounds, salts thereof, or combinations thereof; (d) at least one emulsifier chosen from fatty alcohols, glyceryl esters, or combinations thereof; (e) optionally, at least one $C_3$-$C_8$ polyol chosen from diols and triols; and (f) optionally, at least one fatty compound chosen from vegetable oils.

In yet a further exemplary and non-limiting embodiment, the compositions comprise (a) from about 4% to about 10%, such as from about 5% to about 8%, by weight, of at least one sucrose ester chosen from sucrose stearate, sucrose distearate, sucrose tristearate, sucrose polystearate, sucrose cocoate, sucrose laurate, sucrose palmitate, sucrose dipalmitate, or combinations thereof; (b) from about 0.1% to about 5%, such as from about 1% to about 3%, by weight, of at least one nonionic polysaccharide thickening agent chosen from gums, celluloses, starches, or combinations thereof; (c) from about 0.1% to about 5%, such as from about 1% to about 3%, by weight, of at least one cationic surfactant chosen from monoalkyl quaternary amines, dialkyl quaternary amines, polyquaternium compounds, salts thereof, or combinations thereof; (d) from about 0.1% to about 5%, such as from about 0.5% to about 3%, by weight, of at least one emulsifier chosen from fatty alcohols, glyceryl esters, or combinations thereof; (e) optionally, from about 1% to about 10%, such as from about 3% to about 8%, by weight, of at least one $C_3$-$C_8$ polyol chosen from diols and triols; and (f) optionally, from about 1% to about 10%, such as from about 3% to about 8%, by weight, of at least one fatty compound chosen from vegetable oils.

The disclosure further relates to methods of using the compositions, for example methods of styling hair, methods of elongating curls, methods of lengthening the visual appearance of hair, or methods of reducing frizz, wherein the methods comprise applying the composition to wet, damp, or dry hair. Optionally, the compositions are left on the hair for a period of a few hours to a few days, for example until the hair is washed. The methods provide styling benefits to the hair, such as curl elongation, curl definition, frizz control, smoothness, and/or softness.

The disclosure further relates kits comprising the compositions.

BRIEF DESCRIPTION OF THE FIGURES

The accompanying drawings, which are incorporated herein and constitute part of this specification, illustrate exemplary embodiments of the disclosure, and, together with the general description given above and the description provided herein, serve to explain features of the disclosure.

Figure 1:
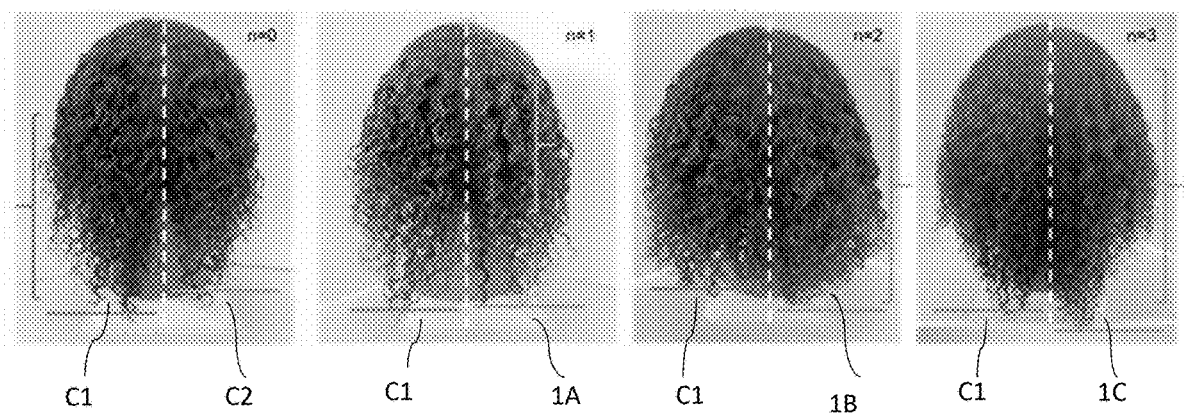
FIG. 1 shows images of a half head study comparing compositions in Table 1.

It is to be understood that the foregoing and following descriptions are exemplary and explanatory only, and are not intended to be restrictive of any subject matter claimed.

DETAILED DESCRIPTION

The disclosure relates to compositions for styling hair, such as for elongation of curls and/or reducing the degree of curliness of hair, as well as to kits comprising the compositions, and methods of using the compositions.

I. Compositions

In various embodiments, the compositions comprise (a) at least one sucrose ester; (b) at least one nonionic polysaccharide thickening agent; (c) at least one cationic surfactant; (d) at least one emulsifier chosen from fatty alcohols, esters, or combinations thereof; (e) optionally at least one $C_3$-$C_8$ polyol chosen from diols and triols; and (f) optionally at least one fatty compound.

Compositions according to the disclosure may improve the hair curl elongation, and in at least some embodiments may provide additional benefits such as curl definition, curl hold, softness, smoothness, and/or frizz control to the hair.

Sucrose Esters

Compositions according to the disclosure comprise at least one sucrose ester. In some embodiments, the compositions may comprise at least two sucrose esters, or more.

Sucrose esters, also known as sugar esters, or sucrose esters of fatty acids, are molecules containing a sucrose moiety attached to a fatty acid. Sucrose esters can be synthesized by the direct esterification of sucrose with a fatty acid, or transesterification reaction of sucrose with a fatty acid ester.

According to some embodiments, suitable sucrose esters may include those having at least one attached fatty acid moiety, and may be chosen from sucrose monoesters, sucrose diesters, sucrose triesters, and sucrose polyesters. Non-limiting examples include sucrose stearate, sucrose distearate, sucrose tristearate, sucrose polystearate, sucrose cocoate, sucrose laurate, sucrose palmitate, sucrose dipalmitate, or mixtures thereof. In some embodiment, the at least one sucrose ester is chosen from sucrose distearate, sucrose tristearate, or a mixture thereof.

In various exemplary embodiments, the at least one sucrose ester may be present in the compositions in an amount of at least 4% by weight, such as at least 5%, at least 6%, at least 6.5%, at least 6.8%, or at least 7% by weight, relative to the total weight of the composition. In exemplary embodiments, the at least one sucrose ester may be present in an amount ranging from about 4% to about 30% by weight, including all subranges therebetween, such as from about 4% to about 25%, from about 4% to about 20%, from about 4% to about 15%, from about 4% to about 10%, from about 5% to about 25%, from about 5% to about 20%, from about 5% to about 15%, from about 5% to about 10%, from about 6% to about 30%, from about 6% to about 25%, from about 6% to about 20%, from about 6% to about 15%, from about 6% to about 10%, from about 6.5% to about 30%, from about 6.5% to about 25%, from about 6.5% to about 20%, from about 6.5% to about 15%, from about 6.5% to about 10%, from about 7% to about 30%, from about 7% to about 25%, from about 7% to about 20%, from about 7% to about 15%, or from about 7% to about 10% by weight relative to the total weight of the composition. In a particular embodiment, the at least one sucrose ester is present in an amount of at least 6.8% by weight, relative to the total weight of the composition, including all ranges and subranges thereof.

Nonionic Polysaccharide Thickening Agents

Compositions according to the disclosure comprise at least one nonionic polysaccharide thickening agent (also referred to as thickener or viscosity modifying agent). Polysaccharide thickening agents are polymers which exhibit monosaccharides or disaccharides as base units. The polysaccharide thickening agents which can be used in the compositions according to the present disclosure include, by way of example only, gums, celluloses, and starches.

Non-limiting examples of gums include acacia, agar, algin, alginic acid, ammonium alginate, amylopectin, calcium alginate, calcium carrageenan, carnitine, carrageenan, dextrin, gelatin, gellan gum, guar gum, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and biosacharide gum. Modified gums or derivatives of gums may also be used, such as, for example, deacylated gellan gum, welan gum, or hydroxypropylated guar gum, such as Jaguar HP 105 sold by Rhodia.

Non-limiting examples of celluloses include hydroxyalkylcelluloses, such as hydroxyethylcelluloses, hydroxypropylmethylcellulose, or hydropropylcelluloses, which may or may not contain a fatty chain. One particularly suitable hydroxypropylmethylcellulose is Methocel F4M sold by Dow Chemicals (INCI name: hydroxypropylmethylcellulose). Celluloses modified with groups comprising one or more nonionic fatty chains that can be used include hydroxyethylcelluloses, preferably nonionic hydroxyethylcelluloses, modified by groups comprising at least one fatty chain, such as alkyl, arylalkyl or alkylaryl groups, or their mixtures, and in which the alkyl groups are preferably C8-C22 alkyl groups, such as the product NATROSOL™ Plus Grade 330 CS (C16 alkyls), sold by Aqualon, corresponding to the INCI name cetylhydroxyethylcellulose, or the product BERMOCOLL® EHM 100 sold by Berol Nobel, and those modified with alkylphenyl polyalkylene glycol ether groups, such as the product AMERCELL POLYMER® HM-1500 (nonylphenyl polyethylene glycol (15) ether) sold by Amerchol that corresponds to the INCI name nonoxynyl hydroxyethylcellulose.

Non-limiting examples of starches include modified starches, starch-based polymers, methylhydroxypropyl starch, potato starch, wheat starch, rice starch, starch crosslinked with octenyl succinic anhydride, starch oxide, dialdehyde starch, dextrin, British gum, acetyl starch, starch phosphate, carboxymethyl starch, hydroxyethyl starch, and hydroxypropyl starch.

In various exemplary embodiments, the total amount of the at least one nonionic polysaccharide thickening agent may vary, but is typically ranges from about 0.1% to about 10%, including all subranges therebetween, such as from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 0.5% to about 2%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, or from about 1% to about 2% by weight, relative to the total weight of the composition, including all ranges and subranges thereof.

Cationic Surfactants

Compositions according to the disclosure comprise at least one cationic surfactant. The term "cationic surfactant" means a surfactant comprising, as ionic or ionizable groups, only cationic groups. In certain embodiments, the cationic surfactants are plant-based and/or organic.

In some embodiments, a cationic surfactant may be chosen from amidoamine compounds (or amidoamines). Examples of amidoamines that are useful in the compositions of the instant disclosure include, but are not limited to the following: oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicamidopropyl dimethylamine, olivamidopropyl dimethylamine, palmitamidopropyl dimethylamine, stearamidoethyldiethylamine, and mixtures thereof.

In some further embodiments, a cationic surfactant can be chosen from monoalkyl quaternary amines, dialkyl quaternary amines, or polyquaternium compounds or salts thereof.

For example, a cationic surfactant may be chosen from Polyquaterium-10 (also called quaternized polyhydroxyethyl cellulose), cetrimonium chloride, behentrimonium chloride, behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Polyquaternium-37 (e.g., under the SALCARE tradename), Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some embodiments, a suitable cationic surfactant may be chosen from polyquaternium 4, polyquaternium 6, polyquaternium 7, polyquaternium 10, polyquaternium 11, polyquaternium 16, polyquaternium 22, polyquaternium 28, polyquaternium-32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, or guar hydroxypropyltrimonium chloride, and mixtures thereof. In an embodiment, the cationic surfactant is chosen from Polyquaternium-67, Polyquaternium-10, Polyquaternium-37, or mixtures thereof. Polyquaternium-37 may be commercially available from BASF under the tradename of SALCARE SC 96 (comprising Polyquaternium-37 (and) Propylene Glycol Dicaprylate/Dicaprate (and) PPG-1 Trideceth-6).

In some embodiments, the at least one cationic surfactant in the compositions comprises behentrimonium chloride. In some further embodiments, the at least one cationic surfactant is chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, or a combination thereof.

Non-limiting examples of cationic surfactants may also include behenalkonium chloride, benzethonium chloride, cetylpyridinium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

In some embodiments, the at least one cationic surfactant is chosen from polyoxyalkylenated primary, secondary, or tertiary fatty amine salts, quaternary ammonium salts, or mixtures thereof. In some cases it is useful to use salts such as chloride salts of the quaternary ammonium compounds. The fatty amines may comprise at least one $C_8$-$C_{30}$ hydrocarbon-based chain.

In some embodiments, suitable quaternary ammonium salts may be those of formula (I):

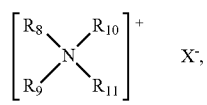

wherein:
groups R8 to R11 are independently chosen from linear or branched aliphatic groups containing from 1 to 30 carbon atoms, or an aromatic group such as aryl or alkylaryl, at least one of the groups R8 to R11 including from 8 to 30 carbon atoms, such as from 12 to 24 carbon atoms, it being possible for the linear or branched aliphatic groups to include heteroatoms such as, for example, oxygen, nitrogen, and/or sulfur, these heteroatoms not being adjacent, and halogens; and $X^-$ is an anion chosen from the group consisting of halides such as bromides, chlorides, iodides, fluorides, phosphates, acetates, lactates, (C1-C4)alkyl sulfates, (C1-C4)alkyl sulfonates or (C1-C4)alkylaryl sulfonates; C1-C30 alkyl, C1-C30 alkoxy, (C2-C6)polyoxyalkylene, C1-C30 alkylamide, (C12-C22)alkyl-(C2C6) alkylamido, (C12-C22)alkyl acetate, and C1-C30 hydroxyalkyl groups.

Mention may be made as exemplary embodiments of formula (V) of tetraalkylammonium halides, such as chlorides, for example dialkyldimethylammonium or alkyltrimethylammonium chlorides in which the alkyl group comprises from 12 to 22 carbon atoms, such as from 14 to 20 carbon atoms. By way of example, behenyltrimethylammonium chloride (behentrimonium chloride), distearyl-dimethylammonium chloride, cetyltrimethylammonium chloride (cetrimonium chloride), or benzyldimethylstearylammonium chloride may be chosen.

In some embodiments, compounds of formula (I) may include palmitylamidopropyltrimethylammonium or stearamidopropyldimethyl-(myristyl acetate)-ammonium halides, such as chlorides, for example the product sold under the name CERAPHYL® 70 by the company Van Dyk.

In certain embodiments, cationic surfactants of formula (I) are preferably chosen from alkyltrimethylammonium halides whose alkyl group includes from 12 to 22 carbon atoms, such as from 14 to 20 carbon atoms, may be chosen. For example, alkyltrimethylammonium chlorides, such as behenyltrimethylammonium chloride and cetyltrimethylammonium chloride, may be particularly useful.

In further embodiments, quaternary ammonium salts of imidazoline of formula (II) may be chosen:

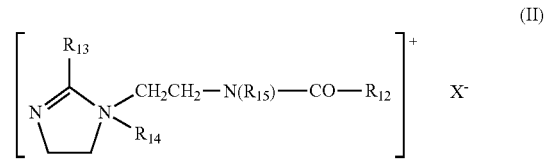

wherein:
R12 represents an alkenyl or alkyl group comprising from 8 to 30 carbon atoms, for example derived from tallow fatty acids,
R13 represents a hydrogen atom, a C1-C4 alkyl group or an alkenyl or alkyl group comprising from 8 to 30 carbon atoms,
R14 represents a C1-C4 alkyl group,
R15 represents a hydrogen atom or a C1-C4 alkyl group, and
$X^-$ is an anion chosen from the group consisting of halides, phosphates, acetates, lactates, (C1-C4)alkyl sulfates, and (C1-C4)alkyl- or (C1-C4)alkylarylsulfonates.

In one exemplary embodiment of formula (II), R12 and R13 represent a mixture of alkenyl or alkyl groups containing from 12 to 21 carbon atoms, derived for example from tallow fatty acids; R14 represents a methyl group; and R15 represents a hydrogen atom. Such a product may be sold, for example, under the name REWOQUAT® W 75 by the company Evonik.

In yet further embodiments, di- or triquaternary ammonium salts of formula (III) may be chosen:

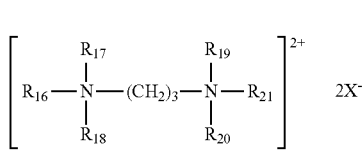

wherein:
- R16 represents an alkyl group comprising from 16 to 30 carbon atoms, which is optionally hydroxylated and/or optionally interrupted with one or more oxygen atoms,
- R17 represents hydrogen, an alkyl group comprising from 1 to 4 carbon atoms, or a group —(CH2)3-N+(R16a)(R17a)(R18a),
- R16a, R17a and R18a, which may be identical or different, represent hydrogen or an alkyl group comprising from 1 to 4 carbon atoms,
- R18, R19, R20, and R21, which may be identical or different, represent hydrogen or an alkyl group comprising from 1 to 4 carbon atoms, and
- X$^-$ is an anion chosen from the group consisting of halides, acetates, phosphates, nitrates, (C1-C4)alkyl sulfates, and (C1-C4)alkyl- and (C1-C4)alkylarylsulfonates, for example methyl sulfate or ethyl sulfate.

Such compounds are, for example, FINQUAT® CT-P (Quaternium 89) and FINQUAT® CT (Quaternium 75), sold by the company Finetex.

In still further embodiments, quaternary ammonium salts containing one or more ester functions, such as those of formula (IV) may be chosen:

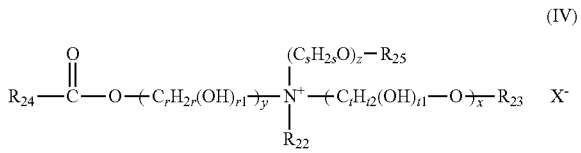

wherein:
- R22 is chosen from C1-C6 alkyl groups and C1-C6 hydroxyalkyl or dihydroxyalkyl groups,
- R23 is chosen from the group R26-C(=O)—; linear or branched, saturated or unsaturated C1-C22 hydrocarbon-based groups; and a hydrogen atom,
- R25 is chosen from the group R28-C(=O)—; linear or branched, saturated or unsaturated C1-C6 hydrocarbon-based groups; and a hydrogen atom,
- R24, R26, and R28, which may be identical or different, are chosen from saturated or unsaturated, linear or branched C7-C21 hydrocarbon-based groups,
- r, s, and t, which may be identical or different, are integers ranging from 2 to 6,
- r1 and t1, which may be identical or different, are equal to 0 or 1,
- y is an integer ranging from 1 to 10,
- x and z, which may be identical or different, are integers ranging from 0 to 10, and
- X$^-$ is an anion;
- it being understood that r2+r1=2r and t1+t2=2t, and that the sum x+y+z ranges from 1 to 15, with the proviso that when x=0 then R23 is chosen from C1-C22 hydrocarbon-based groups, and that when z=0 then R25 denotes a linear or branched, saturated or unsaturated C1-C6 hydrocarbon-based group.

In exemplary embodiments of formula (IV), the alkyl groups R22 may be linear or branched, and are preferably linear. Preferably, R22 denotes a methyl, ethyl, hydroxyethyl or dihydroxypropyl group, and more particularly a methyl or ethyl group. Advantageously, the sum x+y+z ranges from 1 to 10. When R23 is a C1-C22 hydrocarbon-based groups, it may preferably comprise either from 12 to 22 carbon atoms or from 1 to 3 carbon atoms. Advantageously, R24, R26 and R28, which may be identical or different, are chosen from linear or branched, saturated or unsaturated C11-C21 hydrocarbon-based groups, and more particularly from linear or branched C11-C21 alkyl and alkenyl groups. Preferably, x and z, which may be identical or different, are equal to 0 or 1. Optionally, y is equal to 1. Preferably, r, s, and t, which may be identical or different, are equal to 2 or 3, and optionally are equal to 2.

The anion X$^-$ is preferably a halide, optionally chloride, bromide, or iodide, a (C1-C4)alkyl sulfate, a (C1-C4)alkylsulfonate, or a (C1-C4)alkylarylsulfonate, a methanesulfonate, a phosphate, a nitrate, a tosylate, an anion derived from an organic acid such as an acetate or a lactate, or any other anion that is compatible with the ammonium bearing an ester function. In some embodiments, the anion X— is a chloride, a methyl sulfate, or an ethyl sulfate.

For example, the ammonium salts of formula (IV), in which R22 is a methyl or ethyl group, x and y are equal to 1, z is equal to 0 or 1, r, s and t are equal to 2, R23 is chosen from the group R26-C(=O)—, methyl, ethyl, or C14-C22 hydrocarbon-based groups, and a hydrogen atom; R25 is chosen from the group R28-C(=O)—, and a hydrogen atom; R24, R26 and R28, which may be identical or different, are chosen from linear or branched, saturated or unsaturated C13-C17 hydrocarbon-based groups, and preferably from linear or branched, saturated or unsaturated C13-C17 alkyl and alkenyl groups, may be chosen. In one embodiment, the hydrocarbon-based groups are linear.

Among the compounds having formula (IV), mention may be made of salts, especially the chloride or methyl sulfate salts, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These cationic surfactants may be obtained, for example, by direct esterification of triethanolamine, triisopropanolamine, alkyldiethanolamine or alkyldiisopropanolamine, which are optionally oxyalkylenated, with fatty acids or with fatty acid mixtures, such as those of plant or animal origin, or by transesterification of the methyl esters thereof. This esterification may be followed by a quaternization by means of an alkylating agent, such as an alkyl halide, for example, methyl or ethyl halide, a dialkyl sulfate, for example, dimethyl or diethyl sulfate, methyl methanesulfonate, methyl para-toluenesulfonate, glycol chlorohydrin, or glycerol chlorohydrin. Such compounds are sold, for example, under the names DEHYQUART® by the company Henkel, STEPANQUAT® by the company Stepan, NOXAMIUM® by the company CECA or REWOQUAT® WE 18 by the company Evonik.

In some embodiments, the at least one cationic surfactant may be chosen from, for example, a mixture of quaternary ammonium monoester, diester and triester salts with a weight majority of diester salts. In some embodiment, the at least one cationic surfactant may be chosen from the ammonium salts containing at least one ester functional group that are described in patents U.S. Pat. Nos. 4,874,554 and 4,137,180, which are incorporated herein for their entireties. In some embodiment, the at least one cationic surfactant may comprise behenoylhydroxypropyl-trimethylammonium chloride, for example, sold by the company Kao under the name QUARTAM IN® BTC 131.

Suitable cationic surfactants may further include those having a structure in accordance with the general formula provided below:

wherein R4 is a saturated or unsaturated, straight or branched alkyl chain with 8 to 24 carbon atoms, R5 is a straight or branched alkyl chain with 1 to 4 carbon atoms, A is selected from:

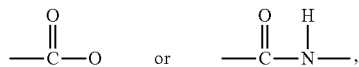

and B is selected from compounds of formula (VI):

wherein $R_6$ and $R_7$, which may be the same or different, are chosen from H, an alkyl chain with 1 to 4 carbon atoms, hydroxyl alkyl chain with 1 to 4 carbon atoms, or di hydroxyl alkyl chain with 2 to 4 carbon atoms; or compounds of formula (VII):

wherein $R_8$ and $R_9$, which can be the same or different, are chosen from an alkyl chain with 1 to 4 carbon atoms, a hydroxyl alkyl chain with 1 to 4 carbon atoms, or a di hydroxyl alkyl chain with 2 to 4 carbon atoms; wherein $R_{10}$ is chosen from an alkyl chain with 1 to 4 carbon atoms, a hydroxyl alkyl chain with 1 to 4 carbon atoms, or a di hydroxyl alkyl chain with 2 to 4 carbon atoms.

In some instances, in formula (V), $R_4$ is saturated or unsaturated, straight or branched alkyl chain with 10 to 24 carbon atoms, more preferably 12 to 22 carbon atoms and $R_5$ is straight or branched alkyl group with 1 to 4 carbon atoms, and A, B, $R_6$ to $R_{10}$ are same as above.

Non-limiting suitable examples include stearyloxypropyl amine, palmityloxypropyl amine, stearyloxypropyldimethyl amine, stearyloxypropyldiethyl amine, stearyloxyethyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, stearamidopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

In some embodiments, a cationic surfactant may be chosen from cationizable surfactants such as fatty alkylamines, preferably, fatty dialkylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyldiethylamine, arachidamidoethyldimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. In some embodiment, a carboxylic acid may be chosen from lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, or mixtures thereof. In some embodiment, lactic acid, tartaric acid or mixtures thereof are used, especially in combination with fatty dimethylamines such as, for example, stearamidopropyl dimethylamine.

Compositions according to the disclosure may be formulated such that two or more cationic surfactants are associated with the same or different balancing anionic ions. For example, at least one of the two or more cationic surfactants may have a chloride ion and/or a sulfate ion. In some embodiments, the two or more cationic surfactants are chosen from cetrimonium chloride, behentrimonium methosulfate, behentrimonium chloride, or combination thereof. In some further embodiments, the two or more cationic surfactants comprise behentrimonium chloride and one or both of behentrimonium methosulfate and cetrimonium chloride.

In various embodiments, the total amount of the at least one cationic surfactant may range up to about 15%, based on the total weight of the composition, including all ranges and subranges therebetween. For instance, the total amount of the at least one cationic surfactant may range from about 0.1% to about 15%, from about 0.1% to about 10%, from about 0.1% to about 5%, from about 0.1% to about 3%, from about 0.5% to about 15%, from about 0.5% to about 10%, from about 0.5% to about 5%, from about 0.5% to about 3%, from about 1% to about 15%, from about 1% to about 10%, from about 1% to about 5%, from about 1% to about 3%, by weight, relative to the total weight of the composition.

Emulsifiers

Compositions according to the disclosure comprise at least one emulsifier chosen from fatty alcohols, esters, or a combination thereof. In some embodiments, the at least on emulsifier is plant-based and/or organic.

Fatty Alcohols

In some embodiments, compositions according to the disclosure comprise at least one emulsifier chosen from fatty alcohols, or derivatives thereof. In certain embodiments, the compositions comprise at least two fatty alcohols.

As used herein, "fatty alcohol" refers to any alcohol with a carbon chain of C5 or greater, such as, for example, C8 or greater, C10 or greater, and C12 or greater. Suitable fatty alcohols according to the disclosure may include, but are not limited to, alkoxylated or non-alkoxylated, saturated or unsaturated, linear or branched, fatty alcohols, for example with from 6 to 30 carbon atoms, such as from 8 to 30 carbon atoms, from 8 to 22 carbon atoms, from 12 to 22 carbon atoms, or from 12 to 18 carbon atoms, including all ranges and subranges therebetween. The fatty alcohols may be liquid or solid. Non-limiting examples of the fatty alcohols and derivatives thereof are found in International Cosmetic Ingredient Dictionary, Sixteenth Edition, 2016, which is incorporated by reference herein in its entirety.

As used herein, "alkoxylated fatty alcohol" refers to any fatty alcohol with a carbon chain of C5 or greater, as defined above, further comprising at least one alkoxy group. For example, the at least one alkoxylated fatty alcohol may have a carbon chain of C8 or greater, C10 or greater, and C12 or greater. Further, for example, the at least one alkoxylated fatty alcohol may be chosen from alkoxylated polymers (including co-, ter- and homo-polymers) derived from alcohols such as glycerol (e.g., polyglyceryl derived from four glycerol molecules). The at least one alkoxy group of the at least one alkoxylated fatty alcohol may, for example, be derived from an alkoxylation reaction carried out with alkylene oxide. Non-limiting examples of at least one alkoxylated fatty alcohol include any fatty alcohol comprising at least one polyethylene glycol ether and any fatty alcohol comprising at least one polypropylene glycol ether.

In some embodiments, the compositions according to the disclosure comprise a liquid fatty alcohol. In some embodiments, the compositions according to the disclosure comprise a solid fatty alcohol. In further embodiments, the compositions according to the disclosure comprise combinations of at least one liquid fatty alcohol and at least one solid fatty alcohol.

According to some embodiments, liquid fatty alcohols that can be used may contain C10-C34, and may have branched carbon chains and/or have branched and/or unsaturated (C=C double bond), and contain from 12 to 40 carbon atoms.

The liquid fatty alcohols may be represented by the formula R—OH, wherein R denotes a C12-C24 branched alkyl group or an alkenyl group (comprising at least one C12-C24 double bond C═C), R being optionally substituted by one or more hydroxy groups. In some embodiments, a liquid fatty alcohol is a branched saturated alcohol. In at least certain embodiments, R does not contain a hydroxyl group. Non-limiting examples of liquid fatty alcohols may include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, and 2-tetradecyl-1-cetanol. In some particular embodiments, the liquid fatty alcohol is 2-octyl-1-dodecanol.

According to further embodiments, solid fatty alcohols that can be used may include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm. The solid fatty alcohols may be soluble, under the same temperature and pressure conditions, in at least one organic solvent (for example ethanol, chloroform, benzene or liquid petroleum jelly) to at least 1% by weight.

The solid fatty alcohols may be represented by the formula R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

Non-limiting examples of solid fatty alcohols include lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol); or mixtures thereof. In some embodiments, the compositions disclosed herein comprise at least one solid fatty alcohol chosen from cetyl alcohol, stearyl alcohol, behenyl alcohol and mixtures thereof such as cetylstearyl or cetearyl alcohol.

Fatty alcohol derivatives that can be used may include methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG-8-ceteth-1, and PPG-10 cetyl ether; and mixtures of all of the foregoing compounds.

In some embodiments, compositions according to the disclosure comprise a fatty alcohol that is hydrogenated (for example, stearyl, lauryl, cetyl, cetearyl). In some embodiments, the fatty alcohol contains one or more double bonds (for example, oleyl). In some embodiments, an emulsifier comprised in the compositions is chosen from decyl alcohol, undecyl alcohol, dodecyl alcohol, myristyl alcohol, lauryl alcohol, cetyl alcohol, stearyl alcohol, cetearyl alcohol (a combination of cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, or a combination thereof. In some embodiments, an emulsifier comprised in the compositions may be chosen from myristyl alcohol, lauryl alcohol, cetyl alcohol, stearyl alcohol, cetearyl alcohol, isostearyl alcohol, oleyl alcohol, isotridecyl alcohol, or a combination thereof.

Thus, without intending to be limiting, the at least one emulsifier may be chosen from C9-C11 alcohols, C12-C13 alcohols, C12-C15 alcohols, C12-C16 alcohols, C14-C15 alcohols, C12-C22 alcohols, arachidyl alcohol, behenyl alcohol, caprylic alcohol, cetearyl alcohol, cetyl alcohol, coconut alcohol, decyl alcohol, hydrogenated tallow alcohol, jojoba alcohol, lauryl alcohol, myristyl alcohol, oleyl alcohol, palm alcohol, palm kernel alcohol, stearyl alcohol, tallow alcohol, tridecyl alcohol, 2-octyldodecanol, isostearyl alcohol, 2-hexyldecanol, 2-heptyldecanol, 2-octyldecanol, caproic alcohol (1-hexanol), enanthic alcohol (1-heptanol), caprylic alcohol (1-octanol), pelargonic alcohol (1-nonanol), capric alcohol (1-decanol), lauryl alcohol (1-dodecanol), or mixtures thereof.

In one embodiment, the at least one fatty alcohol is cetyl alcohol. In one embodiment, the at least one fatty alcohol is cetearyl alcohol. In one embodiment, the at least one fatty alcohol comprises both cetyl alcohol and cetearyl alcohol by way of example. In some embodiments, an emulsifier may be chosen from ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceterarel:h-33, ceteareth-34, ceteareth-40, ceteareth-50, ceteareth-55, ceteareth-60, ceteareth-80, ceteareth-100, laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, lauretih-16, laureth-20, laureth-23, laureth-25, laureth-30, laureth-40, deceth-3, deceth-5, oleth-5, oleth-30, steareth-2, steareth-10, steareth-20, steareth-100, cetylsteareth-12, ceteareth-5, ceteareth-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, C9-C11 pareth-3, C9-C11 pareth-6, C11-C15 pareth-3, C11-C15 pareth-5, C11-C15 pareth-12, C11-C15 pareth-20, C12-C15 pareth-9, C12-C15 pareth-12, C22-C24 pareth-33, or a mixture thereof.

Glyceryl Esters (Glycerol Esters)

In some embodiments, compositions according to the disclosure comprise at least one emulsifier chosen from one glyceryl (or glycerol) esters, or derivatives thereof.

The at least one glyceryl ester may have a carbon chain of 8 to 24 carbons, and may be chosen from: i) esters of an oligomeric glycerol; ii) the arachidyl propionate sold under the trade mark WAXENOL 801 by Alzo; iii) phytosterol esters, triglycerides of fatty acids and derivatives thereof, such as hydrogenated cocoglycerides; iv) noncrosslinked polyesters resulting from the poly condensation between a linear or branched C4-C50 dicarboxylic acid or polycarboxylic acid and a C2-C50 diol or polyol; v) aliphatic esters of an ester resulting from the esterification of an aliphatic hydroxycarboxylic acid ester with an aliphatic carboxylic acid; or vi) a mixture thereof.

Non-limiting examples of the esters of an oligomeric glycerol include diglycerol, such as the condensates of adipic acid and of glycerol, for which a portion of the hydroxyl groups of the glycerols have reacted with a mixture of fatty acids, such as steric acid, capric acid, stearic and isostearic acid, and 12-hydroxystearic acid, such as those sold under the trade mark SOFTISAN 649 by the company Cremer Oleo or under the trademark SP SUPERMOL B MBAL-SS-(RB) by the company Croda, such as bis-diglyceryl polyacyladipate-2, or may be bis-diglyceryl polyacyladipate-1.

In certain exemplary embodiments, the glycerol esters may be polyglycerol esters of fatty acids (polyglyceryl esters) having a structure in accordance with the following formula (VIII):

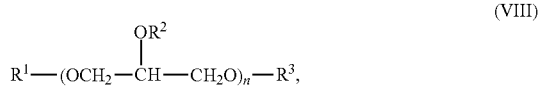

$$R^1-(OCH_2-\underset{\underset{R^2}{|}}{CH}-CH_2O)_n-R^3, \tag{VIII}$$

wherein n is from 2 to 20, from 2 to 10, or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, $C_1$-$C_{20}$, $C_1$-$C_{16}$, or $C_1$-$C_{10}$.

Non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, and polyglyceryl-10 stearate.

In some embodiments, the at least one emulsifier comprises at least one glyceryl ester chosen from esters of an oligomeric glycerol, arachidyl propionate, phytosterol esters, triglycerides of fatty acids and derivatives thereof, noncrosslinked polyesters resulting from the poly condensation between a linear or branched C4-C50 dicarboxylic acid or polycarboxylic acid and a C2-C50 diol or polyol, aliphatic esters of an ester resulting from the esterification of an aliphatic hydroxycarboxylic acid ester with an aliphatic carboxylic acid, and a mixture thereof. Non-limiting examples of glyceryl esters include bis-diglyceryl polyacyladipate-1, bis-diglyceryl polyacyladipate-2, glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, glyceryl dioleate, glyceryl distearate, glyceryl laurate, or a mixture thereof. In one embodiment, the at least one emulsifier is chosen from glyceryl stearate, bis-diglyceryl polyacyladipate-1, bis-diglyceryl polyacyladipate-2, or a mixture thereof. In another embodiment, at least one emulsifier is chosen from glyceryl esters comprising bis-diglyceryl polyacyladipate-1 and/or bis-diglyceryl polyacyladipate-2, and optionally, a second glyceryl ester. In one other embodiment, the at least one emulsifier comprises a glyceryl ester that is glyceryl stearate, and optionally, a second glyceryl ester. In a preferred embodiment, the composition comprises bis-diglyceryl polyacryladipate-1 and/or bis-diglyceryl polyacryladipate-2, and optionally at least one additional emulsifier.

Non-Glyceryl Esters

In some embodiments, compositions according to the disclosure may also include an ester other than glyceryl esters (non-glyceryl esters). In some cases, the ester other than glyceryl ester is chosen from isopropyl esters, cetyl esters, or a mixture thereof. Non-limiting examples of isopropyl esters include isopropyl myristate, isopropyl laurate, isopropyl oleate, isopropyl palmitate, and isopropyl stearate. In some embodiments, the ester that is not a glyceryl ester may be chosen from isopropyl myristate, cetyl esters, isopropyl palmitate, or a mixture thereof.

The ester other than glyceryl ester may also be chosen from a fatty ester. Non-limiting examples of fatty esters may include ethoxylated fatty esters, such as the adducts of ethylene oxide with esters of lauric acid, palmitic acid, stearic acid or behenic acid, and mixtures thereof. Exemplary suitable fatty esters may include those containing from 9 to 100 oxyethylene groups, such as PEG-9 to PEG-50 laurate (as the INCI names: PEG-9 laurate to PEG-50 laurate); PEG-9 to PEG-50 palmitate (as the INCI names: PEG-9 palmitate to PEG-50 palmitate); PEG-9 to PEG-50 stearate (as the INCI names: PEG-9 stearate to PEG-50 stearate); PEG-9 to PEG-50 palmitostearate; PEG-9 to PEG-50 behenate (as the INCI names: PEG-9 behenate to PEG-50 behenate); polyethylene glycol 100 EO monostearate (INCI name: PEG-100 stearate); and mixtures thereof.

According to the disclosure, the total amount of the at least one emulsifier chosen from fatty alcohols, esters, and/or derivatives thereof, or the amount of each of the individual fatty alcohols, esters, and/or derivatives thereof, in the composition may range up to about 15%, such from about 0.01% up to about 15% by weight, based on the total weight of the composition. By way of non-limiting example, any of the at least one emulsifier chosen from fatty alcohols, esters, or combinations thereof, may be present in the composition with an amount ranging from about 0.01% to about 9%, about 0.01% to about 8%, about 0.01% to about 6%, about 0.01% to about 5%, about 0.01% to about 4%, about 0.01% to about 3%, about 0.01% to about 2%, about 0.01% to about 1%, or any suitable combination, sub-combination, range, or sub-range thereof by weight, based on the weight of the composition.

In further embodiments, the at least one emulsifier may be present in an amount ranging from about 0.1% to about 10%, about 0.1% to about 9%, about 0.1% to about 7%, about 0.1% to about 6%, about 0.1% to about 4%, about 0.1% to about 2%, from about 0.5% to about 10%, about 0.5% to about 9%, about 0.5% to about 7%, about 0.5% to about 6%, about 0.5% to about 4%, about 0.5% to about 2%, or any suitable combination, sub-combination, range, or sub-range thereof by weight, based on the weight of the composition. Thus, any one of the at least one emulsifier may be present, by weight, based on the total weight of the composition, from about 0.1, 0.2, 0.3, 0.4, 0.5, 0.6, 0.7, 0.8, 0.9, 1, 2, 3, 4, 5, 6, 7, 8, 9 weight percent to about 10 weight percent, including increments and ranges therein and there between. In a particular embodiment, the at least one emulsifier is present in an amount ranging from about 0.5% to about 10%.

$C_3$-$C_8$ Polyols

Optionally, compositions according to the disclosure comprise at least one $C_3$-$C_8$ polyol chosen from diols and triols. The at least one $C_3$-$C_8$ polyol chosen from diols and triols may be linear or branched, saturated or unsaturated, and substituted or unsubstituted. Any stereoisomer of the $C_3$-$C_8$ polyols chosen from diols and triols may be used.

In various exemplary embodiments, the $C_3$-$C_8$ polyols chosen from diols and triols may be chosen from glycols such as ethylene glycol, propylene glycol, butylene glycol, hexylene glycol, pentylene glycol, 1,3-propanediol, diethylene glycol, triethylene glycol, tetraethylene glycol, pentaethylene glycol, dipropylene glycol, caprylyl glycol, glycerin, diglycerin, and mixtures thereof.

In other embodiments, the $C_3$-$C_8$ polyols chosen from diols and triols may be chosen from, for example, propanediol, butanediol, pentanediol, hexanediol, heptanediol, octanediol, 1,2,6-hexanetriol, 1,2,4-butanetriol, trimethylolpropane, 2-butene-1,4-diol, 2-ethyl-1,3-hexanediol, 2-methyl-2,4-pentanediol, caprylyl glycol, 1,2-hexanediol, 1,2-pentanediol, 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, 2-ethyl-1,3-hexanediol, and 4-methyl-1,2-pentanediol.

In some embodiments, the compositions according to the disclosure comprise at least two $C_3$-$C_8$ polyols chosen from diols and triols. As one non-limiting example, a composition according to the disclosure may comprise a combination of glycerin and caprylyl glycol.

If present, the total amount of the at least one $C_3$-$C_8$ polyol chosen from diols and triols can be about 3% or more, about 4% or more, or about 5% or more, by weight, based on the total weight of the composition. In some embodiments, the at least one $C_3$-$C_8$ polyol chosen from diols and triols is present in the composition with a total amount ranging from about 3% to about 20%, such as from about 3% to about 15%, from about 3% to about 10%, from about 3% to about 9%, from about 3% to about 8%, from about 3% to about 7%, from about 3% to about 6%, from about 4% to about 20%, from about 4% to about 15%, from about 4% to about 10%, from about 4% to about 9%, from about 4% to about 8%, from about 4% to about 7%, from about 4% to about 6%, from about 5% to about 20%, from about 5% to about 15%, from about 5% to about 10%, from about 5% to about 9%, from about 5% to about 8%, from about 5% to about 7%, or from about 5% to about 6% by weight, relative to the total weight of the composition.

In one exemplary and non-limiting embodiment, the at least one $C_3$-$C_8$ polyol chosen from diols and triols is present in an amount of about 5% or more by weight, relative to the total weight of the composition, and comprises glycerin.

Fatty Compounds

Compositions according to the disclosure may optionally comprise at least one fatty compound. Non-limiting examples of fatty compounds include vegetable oils, hydrocarbon-based oils of mineral or synthetic origin, fatty acids and esters thereof, waxes, triglycerides, lanolins, alkanes, petrolatum, paraffins, and fatty alcohols other than those described above, as well as derivatives of the foregoing.

Vegetable oils are oils derived from a plant, for example, oils from seeds or fruits. In some embodiments, vegetable oils that may be used according to the disclosure may include a hydrocarbon-based oil of plant origin and/or vegetable origin. Non-limiting examples of such vegetable oils include acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, castor oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, cannabis oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, grapeseed oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil.

In some embodiments, the fatty compound may include an oil chosen from glyceride triesters, which are generally triesters of fatty acids and of glycerol, the fatty acids of which can have varied chain lengths from $C_4$ to $C_{24}$, it being possible for these chains to be saturated or unsaturated and linear or branched. Non-limiting examples of these oils include wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

In some embodiments, vegetable oils that may be used according to the disclosure may include an essential oil. Such an essential oil may be chosen from sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, ylang, or a mixture thereof.

In some embodiments, compositions according to the disclosure comprise *Ricinus communis* (castor) seed oil, butyrospermum parkii (shea) butter, or a combination thereof.

Exemplary and non-limiting hydrocarbon-based oils of mineral or synthetic origin may include volatile or non-volatile liquid paraffins and derivatives thereof, petroleum jelly, mineral oil, perhydrosqualene, polydecenes, isohexadecane, isododecane, hydrogenated polyisobutene, or mixtures thereof.

Waxes useful according to the disclosure include waxes of natural origin, for instance beeswax, carnauba wax, candelilla wax, ouricoury wax, Japan wax, cork fiber wax, sugar cane wax, paraffin wax, lignite wax, microcrystalline waxes, lanolin wax, montan wax, ozokerites and hydrogenated oils, for instance hydrogenated jojoba oil, or waxes of synthetic origin, for instance polyethylene waxes derived from the polymerization of ethylene, waxes obtained by Fischer-Tropsch synthesis, esters of fatty acids and of glycerides that are solid at 40° C., or silicone waxes such as polypropylsilsesquioxane wax substituted with alkyl units having at least 30 carbons.

Exemplary and non-limiting fatty acids may include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein, and salts of these fatty acids. Non-limiting examples include lauric acid, palmitic acid, stearic acid, behenic acid, arichidonic acid, oleic acid, isostearic acid, sebacic acid, and mixtures thereof, as well as esters thereof.

The total amount of the at least one fatty compound that may be included in various embodiments may range from about 0.01% to about 15%, including all subranges therebetween, such as from about 0.01% to about 10%, from about 0.01% to about 8%, from about 0.01% to about 6%, from about 0.01% to about 4%, from about 0.01% to about 2%, from about 0.1% to about 15%, from about 0.1% to about 10%, from about 0.1% to about 8%, from about 0.1% to about 6%, from about 0.1% to about 4%, from about 0.1% to about 2%, from about 0.5% to about 15%, from about 0.5% to about 10%, from about 0.5% to about 5%, from about 0.5% to about 4%, from about 0.5% to about 2%, from about 1% to about 15%, from about 1% to about 10%, from about 1% to about 8%, from about 1% to about 6%, or from about 1% to about 4%, by weight, based on the total weight of the composition. In some particular embodiments, the at least one fatty compound comprises *Ricinus communis* (castor) seed oil, butyrospermum parkii (shea) butter, or a combination thereof in an amount of about 1% to 10% by weight, such as about 3% to about 7% or about 4% to about 6%, relative to the total weight of the composition.

Solvents

Compositions according to the disclosure may comprise a cosmetically acceptable solvent. The solvent may be chosen from water, non-aqueous solvents, or mixtures thereof.

In some embodiments, the solvent comprises, consists essentially of, or consists of water. The total amount of water in the compositions may vary depending on the type of composition and the desired consistency, viscosity, etc.

In certain embodiments, the composition comprises one or more non-aqueous solvents, other than or in addition to ingredients discussed above. For example, $C_{1-4}$ alcohols, organic solvents, fatty alcohols, fatty ethers, fatty esters, polyols other than those described above, glycols, vegetable oils, mineral oils, liposomes, laminar lipid materials, or any a mixture thereof. Non-limiting examples of solvents which may be used include alkane polyols such as, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; alkyl alcohols having 1 to 4 carbon atoms such as ethanol, methanol, butanol, propanol, and isopropanol (isopropyl alcohol); glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof. At least in some embodiments, the compositions contain isopropyl alcohol.

The solvent may be present in the composition in an amount ranging from about 50% to about 98% by weight, relative to the total weight of the composition, including all ranges and subranges therebetween. For example, in one embodiment, the total amount of solvent may be about 50% to about 95%, about 60% to about 95%, about 70% to about 95%, about 70% to about 90%, about 75% to 95%, or about 75% to 90% by weight, relative to the total weight of the composition. In certain embodiments, the solvent is primarily comprised of water, such as from about 90% to about 99%, or about 95% to about 99%, of the total solvent.

Additional Components

Compositions according to the disclosure may optionally comprise any additional or auxiliary component suitable for use in such compositions. Such components may include, but are not limited to, conditioning agents, dyes/pigments, moisturizing agents, fillers, structuring agents, shine agents, antioxidants, penetrants, sequestrants, fragrances, buffers, dispersants, plant extracts, preserving agents (preservatives), opacifiers, sunscreen agents, pH adjusting agents, vitamins, and antistatic agents.

Optional additional auxiliary components may be present in an amount ranging up to about 15%, such as from about 0.01% to about 15% or about 0.1% to about 10% by weight, relative to the total weight of the composition.

Optionally, the compositions may comprise up to about 100% biodegradable, sustainable, and/or environmentally friendly raw materials, such as up to about 99%, up to about 98%, up to about 97%, up to about 96%, or up to about 95%.

In various embodiments, the compositions may have a pH less than or equal to about 7. For example, the pH of the compositions may range from about 2 to about 6, such as from about 3 to about 5, or from about 3.5 to about 4.5, including all ranges and subranges therebetween.

Compositions according to the disclosure may not require a reducing agent, such as a reducing agent with a base. As such, in some embodiments, the compositions are free or essentially free of a reducing agent.

Compositions according to the disclosure are typically in the form of a liquid, cream, paste, gel, foam, such as mousse, lotion, but are not limited to these forms. The term "gel" is generally understood to mean a soft, semi-solid, or solid-like material that exhibits low to no flow under steady state. In some embodiments, the compositions may be formulated as aerosol type products. In some embodiments, the compositions are non-aerosol type product. When the compositions are formulated as aerosol type products, the compositions may further comprise a propellant.

The viscosities of the compositions are not limited, but by way of example only, in certain embodiments the viscosities may range from about 2 to about 5 Pa·s, such as about 2.3 to about 4.8 Pa·s, or about 2.4 to about 4.7 Pa·s, including all ranges and subranges therebetween, when measured using a rheometer at 25° C. (spindle #4, 30 sec).

II. Kits

The disclosure also relates to kits comprising the compositions disclosed herein.

Kits according to the disclosure may comprise a first container containing a composition disclosed herein. Optionally, kits according to the disclosure may comprise a second container. As an example, a kit may optionally further comprise a second container comprising a hair treatment composition other than the compositions disclosed herein, including but not limited to a hair-treatment rinse, a shampoo, a hair conditioner, a hair-color-toning composition, a hair lightening composition, a hair coloring composition, a hair waving composition, a hair combing device, or a skin care or make-up composition. A kit may also comprise an application instructions and/or a composition/formulation information.

In further exemplary embodiments, the kits may contain at least one first container containing a composition according to the disclosure and at least one second container configured to dispense or apply the compositions described herein. Thus, in one embodiment, a first container may be a jar or a bottle containing a composition according to the disclosure, and a second container may be a squeezable tube or bottle, configured to be filled with the composition in order to apply the composition to the hair to be treated.

Container(s) configured to dispense or apply the compositions may, in various embodiments, be disposable or refillable.

III. Methods

The present disclosure also relates to methods for improving elongation of curly hair by the use of the compositions described herein. The methods generally comprise applying any of the compositions according to the disclosure to the hair.

Compositions according to the disclosure are typically used for providing a visible elongation benefit to curly hair, or for improving the elongation of hair curls. The compositions may be useful in a variety of settings, either for chemically treated or untreated hair, and/or for natural or unnatural curls. The degree of curliness or curl type of the hair may vary and is not limited. For example, the curls of hair been treated by the compositions disclosed herein may range from slightly wavy to very kinky and coily hair, and may have different textures and colors.

In addition to improving elongation of hair curls, the compositions may also be used to provide a variety of desirable sensory benefits, for example, curl definition, curl hold, moisture, smoothness, softness, good bounce, good shine, and/or anti-frizz, to the hair. As such, the compositions are useful in styling (which includes shaping) hair while also caring for hair, conditioning hair, and/or imparting one or more above described sensory benefits to the hair.

Typically, methods according to the disclosure may include applying an effective amount of a composition disclosed herein to hair having curls, when the hair is dry, wet, damp, or moist. The hair may have either natural or unnatural hair. As used herein, the term "effective amount" refers to an amount sufficient to provide a desired elongation effect to the hair, taking into account the degree of curliness, the length, the volume, and the texture of the hair. In general, from about 0.5 grams to about 50 grams of product is applied to the hair, depending on the specific product formulation, hair length, hair volume, and hair style type. The composition applied to the hair may be distributed evenly by combing through with fingers or a means such as a comb or the like. The composition may then be dried, for example air-dried. The composition may be allowed to remain on the hair as a leave-in product for any period of time as needed, for example, from about a few seconds (e.g. 1, 3, 5, or 10 seconds) to about 10, 20, or 30 minutes, or longer, such as a few hours or a few days, or until the next washing or rinsing of the hair.

In some embodiments, before applying the composition to the hair, the hair may be first cleansed with a commercially available shampoo, or rinsed with water. The composition is then applied to the washed or rinsed hair when the hair is wet, damp, or moist. In some other embodiments, before applying the composition to dry hair, the hair can optionally be moistened, damped, or wetted by water spray or using a wet towel, or by applying other treatment compositions that make the hair moist, damp, or wet.

Alternatively, in some embodiments, the compositions according to the disclosure may be first applied to dry hair, and then water or a cosmetically acceptable compositions are applied to the hair to moist, damp, or wet the hair when the compositions according to the disclosure are remained thereon. The hair that has been applied with the compositions disclose herein may be air-dried without further treatment of the hair, including rinsing or washing the hair.

In some embodiments, the methods may optionally include braiding and/or twisting out the hair to make curls, before or after application of the compositions disclosed herein. In some embodiments, methods according to the disclosure do not require shaping or styling the hair before, during, and/or after applying the compositions. A tension to the hair is generally not needed. As such, in some embodiments, before, during, or after applying the compositions, the hair is not stretched by a mechanical means.

In some embodiments, after application of the compositions disclosed herein, the hair may be shaped or styled as needed, such as be twisted or the like. In some embodiments, the hair treated with the compositions may be twisted within 30 minutes, or within 20 minutes, while the hair is wet or damp.

Methods according to the disclosure generally do not require the use of a reducing agent, including a base, or heating the hair for stretching the hair curls or elongating the hair curls. As such, in some embodiments, the method does not including using a reducing agent, or a base, and/or does not including heating the hair.

In some embodiments, a composition disclosed herein is used alone to treat the hair, without the use of other hair treatment compositions. In some other embodiments, the compositions may be applied to the hair before, during, or after another hair treatment or styling composition, such as (e.g. a conditioner, a mask, a cream, a lotion, a gel, a coloring composition, etc.), is applied to the hair. As such, a composition disclosed herein may be applied to the hair and layered with another composition that is also applied to the hair.

In various embodiments, the methods of treating hair with the compositions according to the disclosure, impart various long-lasting benefits described above to the hair, without a greasy feel or flaking, relative to hair not having been treated with a composition according to the disclosure. The term "long-lasting," as used herein, means that the elongation effect and other benefits imparted to the hair may remain a desired length of time, such as a few hours, a few days, or until the hair is rinsed or washed.

Having described the many embodiments of the present invention in detail, it will be apparent that modifications and variations are possible without departing from the scope of the disclosure defined in the appended claims. Furthermore, it should be appreciated that all examples in the present disclosure, while illustrating many embodiments of the disclosure, are provided as non-limiting examples and are, therefore, not to be taken as limiting the various aspects so illustrated. It is to be understood that all definitions herein are provided for the present disclosure only.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the compositions.

In this application, the use of the singular includes the plural unless specifically stated otherwise. The singular forms "a," "an," "the," and "at least one" are understood to encompass the plural as well as the singular unless the context clearly dictates otherwise, and these expressions, as well as the expression "one or more" which means "at least one," are expressly intended to include the individual components as well as mixtures/combinations thereof. Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

As used herein, the phrases "and mixtures thereof," "and a mixture thereof," "and combinations thereof," "and a combination thereof," "or mixtures thereof," "or a mixture thereof," "or combinations thereof," and "or a combination thereof," are used interchangeably to denote that the listing of components immediately preceding the phrase, such as "A, B, C, D, or mixtures thereof" signify that the component(s) may be chosen from A, from B, from C, from D, from A+B, from A+B+C, from A+D, from A+C+D, etc., without limitation on the variations thereof. Thus, the components may be used individually or in any combination thereof.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. All ranges and amounts given herein are intended to include sub-ranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. The term "about" is used herein to indicate a difference of up to +/−10% from the stated number, such as +/−9%, +/−8%, +/−7%, +/−6%, +/−5%, +/−4%, +/−3%, +/−2%, or +/−1%. Likewise, all endpoints of ranges are understood to be individually disclosed, such that, for example, a range of 1:2 to 2:1 is understood to disclose a ratio of both 1:2 and 2:1.

"Active material" as used herein with respect to the percent amount of an ingredient or raw material, refers to 100% activity of the ingredient or raw material.

All amounts given herein are relative to the amount of active material, unless otherwise indicated.

All percentages, parts and ratios herein are based upon the total weight of the compositions of the present disclosure, unless otherwise indicated.

As used herein, the terms "applying a composition onto keratin materials" and "applying a composition onto hair" and variations of these phrases are intended to mean contacting the keratin materials including hair and skin, with at least one of the compositions of the disclosure, in any manner. It may also mean contacting the keratin materials in an effective amount.

Unless otherwise indicated, all percentages herein are by weight, relative to the weight of the total composition.

As used herein, the term "styling" is intended to include "shaping."

As used herein, the term "curly hair" refers to any hair including a curl. The curl may be natural or unnatural, i.e., formed by chemical treatment or physical treatment of the hair. The degree of curliness of the hair may vary and is not limited.

As used herein, hair with improved or enhanced curl definition may have curls with a shape that has a clean ringlet appearance rather than being frizzy, curls that appear more individualized, curls that are more closed in appearance, and/or curls that have an improved visual appearance of the hair color and/or highlights.

As used herein, the terms "elongating" and "stretching" curly hair are interchangeable, and both refer to reducing the degree of curliness and/or tightness of curls of the hair, and "improving the elongation of hair curls" and variants thereof means that the length of the hair appears closer to the actual, uncurled length of the hair.

A "leave-in" composition or product refers to a composition such as a hair-treatment composition that is not rinsed and/or washed away with water or acceptable solvent after the application of the composition onto the keratin fiber, such as hair; instead, the composition is allowed to remain on the keratin fibers for a period of time as desired, such from 1 hour, 2 hours, 3 hours, 4 hours, up to 8 hours, overnight, or as long as needed, until next time of washing or rinsing the keratin fibers.

As used herein, the term "organic" means a material that is produced substantially without or essentially without the use of synthetic materials.

As used herein, the term "polyol" refers to an organic molecule comprising more than two free hydroxyl groups.

The terms "substantially without" or "essentially without" as used herein means the specific material may be used in a manufacturing process in small amounts that do not materially affect the basic and novel characteristics of the compositions according to the disclosure. The terms may also mean that the specific material is not used in a manufacturing process but may still be present in a raw material that is included in the composition.

As used herein, the term "salts" refers to throughout the disclosure may include salts having a counter-ion such as an alkali metal, alkaline earth metal, or ammonium counterion. This list of counterions, however, is non-limiting.

As used herein, the term "stable" indicates that the composition does not exhibit phase separation and/or crystallization for a period of time, for example, for at least 1 day (24 hours), one week, one month, or over a year. "Stable"

also refers to a composition which, after two months of storage at 25 to 45° C., shows no change in appearance, color, odor, or viscosity.

As used herein, the term "substantially free" or "essentially free" as used herein means the specific material may be present in small amounts that do not materially affect the basic and novel characteristics of the compositions according to the disclosure. For instance, there may be less than 2% by weight of a specific material added to a composition, based on the total weight of the compositions (provided that an amount of less than 2% by weight does not materially affect the basic and novel characteristics of the compositions according to the disclosure. Similarly, the compositions may include less than 2%, less than 1.5%, less than 1%, less than 0.5%, less than 0.1%, less than 0.05%, or less than 0.01%, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure. The term "substantially free" or "essentially free" as used herein may also mean that the specific material is not added to the composition but may still be present in a raw material that is included in the composition.

As used herein, the term "surfactants," as well as any specifically-identified surfactants, includes salts of the surfactants even if not explicitly stated.

As used herein, the term "surfactant system" refers to a combination of different surfactants. For example, the term "anionic surfactant system" refers to one anionic surfactant or a combination of different anionic surfactants, and the term "nonionic surfactant system" refers to one nonionic surfactant or a combination of different nonionic surfactants.

As used herein, the term "synthetic" means a material that is not of natural origin. The term "natural" and "naturally-sourced" means a material of natural origin, such as derived from plants, which also cannot be subsequently chemically or physically modified. "Plant-based" means that the material came from a plant.

As used herein, the term "treat" (and its grammatical variations) refers to the application of the compositions of the present disclosure onto the surface of keratin materials, such as hair.

Unless otherwise expressly stated, it is in no way intended that any method set forth herein be construed as requiring that its steps be performed in a specific order. Accordingly, where a method claim does not expressly recite an order to be followed by its steps or it is not specifically stated in the claims or descriptions that the steps are to be limited to a specific order, it is no way intended that any particular order be inferred.

EXAMPLES

The following examples are intended to be non-limiting and explanatory in nature only. In the Examples, amounts are expressed in percentage by weight (wt %) of active materials, relative to the total weight of the composition.

Example 1—Compositions

The inventive and comparative compositions set forth in Table 1 below were prepared.

TABLE 1

| | Compositions | | | | |
|---|---|---|---|---|---|
| | Inventive Compositions | | | Comparative Compositions | |
| INCI Name | 1A | 1B | 1C | C1 | C2 |
| HYDROGENATED STARCH HYDROLYSATE | | | | 7.0 | |
| SUCROSE | | | | | 7.0 |
| SUCROSE STEARATE | 6.8 | | | | |
| SUCROSE DISTEARATE | | 7.0 | | | |
| SUCROSE TRISTEARATE | | | 7.0 | | |
| HYDROXYPROPYL GUAR | 1.25 | 1.25 | 1.25 | 1.25 | 1.25 |
| GLYCERYL STEARATE SE | 1.0 | 1.0 | 1.0 | 1.0 | 1.0 |
| CETYL ESTERS | 0.25 | 0.25 | 0.25 | 0.25 | 0.25 |
| CETEARYL ALCOHOL | 3.0 | 3.0 | 3.0 | 3.0 | 3.0 |
| CAPRYLYL GLYCOL | 0.3 | 0.3 | 0.3 | 0.3 | 0.3 |
| GLYCERIN | 5.0 | 5.0 | 5.0 | 5.0 | 5.0 |
| BEHENTRIMONIUM CHLORIDE | 1.58 | 1.58 | 1.58 | 1.58 | 1.58 |
| BIS-DIGLYCERYL POLYACYLADIPATE-2 | 1.0 | 1.0 | 1.0 | 1.0 | 1.0 |
| *BUTYROSPERMUM PARKII* (SHEA) BUTTER | 2 | 2 | 2 | 2 | 2 |
| *RICINUS COMMUNIS* (CASTOR) SEED OIL | 2.0 | 2.0 | 2.0 | 2.0 | 2.0 |
| ADDITIVES (fragrance, preservatives, pH adjusters) | 1.6 | 1.6 | 1.6 | 1.6 | 1.6 |
| SOLVENT (water + non-aqueous solvents) | QS to 100 | QS to 100 | QS to 100 | QS to 100 | QS to 100 |

Each of compositions 1A-1C and C1-C2 was prepared by mixing the solvents and hydroxypropyl guar in a tank of a homogenizer to form a first mixture, followed with heating to about 70° C., and then adding behentrimonium chloride to form a first mixture. Second, in a separate container, caprylyl glycol, bis-diglyceryl polyacyladipate-2, shea butter, castor seed oil, cetearyl alcohol, glyceryl stearate SE, and cetyl esters, were mixed to form a second mixture and heated to about 70° C. When both the first mixture and the second mixture reached a temperature of about 70° C., the second mixture was added to the first mixture in the tank of the homogenizer, and homogenized until a homogenized mixture was obtained. The homogenized mixture was cooled to room temperature and the polyols, diols, and/or triols, as well as the fragrance and preservatives, were added with mixing at about 45° C. The final mixture was cooled to room temperature to obtain the composition.

Compositions 1A-1C and C1-C2 were in the form of a cream with viscosities at 25° C. of about 2.3 Pa·s to about 4.8 Pa·s (M4) (spindle #4, 30 sec), and relative densities of about 0.98 mass per unit to about 1.02 mass per unit. The pH at 25° C. was measured to be in the range of about 3.5 to about 4.5. These compositions were stable when stored at room temperature or at a temperature up to about 45° C. for over 12 months.

Example 2—Demonstration of Effects on Hair

A half head study was conducted on mannequin heads having curly hair to assess the curl elongation effect of compositions including a sucrose ester according to the disclosure, compared to comparative compositions not including a sucrose ester.

In this study, example compositions 1A-1C and comparative composition C2 from Table 1 were tested on mannequin heads against comparative composition C1 from Table 1.

For each mannequin head, the hair of the mannequin head was first cleansed with a commercially available shampoo. While the hair was still wet or damp, a sufficient amount of C1 was applied to one half-head of each mannequin and distributed evenly onto the hair with the fingers. Approximately the same amount of one of compositions 1A-1C or C2 was then applied to the other half of the head, and similarly distributed evenly. The hair of the mannequin was then allowed to air dry. FIG. 1 shows images of each comparison.

As shown in FIG. 1, the hair treated with comparative composition C2 appeared shorter than the hair treated with comparative composition C1. An elongation effect in the curls can be seen in the hair treated with each of compositions 1A-1C, with the hair of compositions 1B and 1C showing the greatest effect.

The Example demonstrated that compositions according to the present disclosure, which comprise sucrose esters, improve the elongation of hair curls.

Example 3—Demonstration of Effect of Concentration of Sucrose Ester

In order to demonstrate the beneficial effects of compositions according to the disclosure could be achieved across a range of concentrations, the following compositions containing varying amounts of sucrose distearate (2A-2E) and a comparative composition without sucrose distearate (C3) were prepared.

TABLE 2

Testing Compositions

| INCI Name | C3 | 2A | 2B | 2C | 2D | 2E |
|---|---|---|---|---|---|---|
| Sucrose Distearate | 0 | 7 | 15 | 20 | 25 | 30 |
| Water | QS to 100 | QS to 100 | QS to 100 | QS to 100 | QS to 100 | QS to 100 |
| Average curl shrinkage after 24 hours | 13.0% | 10.4% | 9.2% | 8.6% | 7.6% | 8.0% |

Each of compositions 2A-2E and C3 was tested on three hair swatches. Each hair swatch was first washed with a commercially available shampoo. While the swatches were still wet or damp, equal amounts of a testing composition was applied to each hair swatch and distributed evenly.

Figure 2:
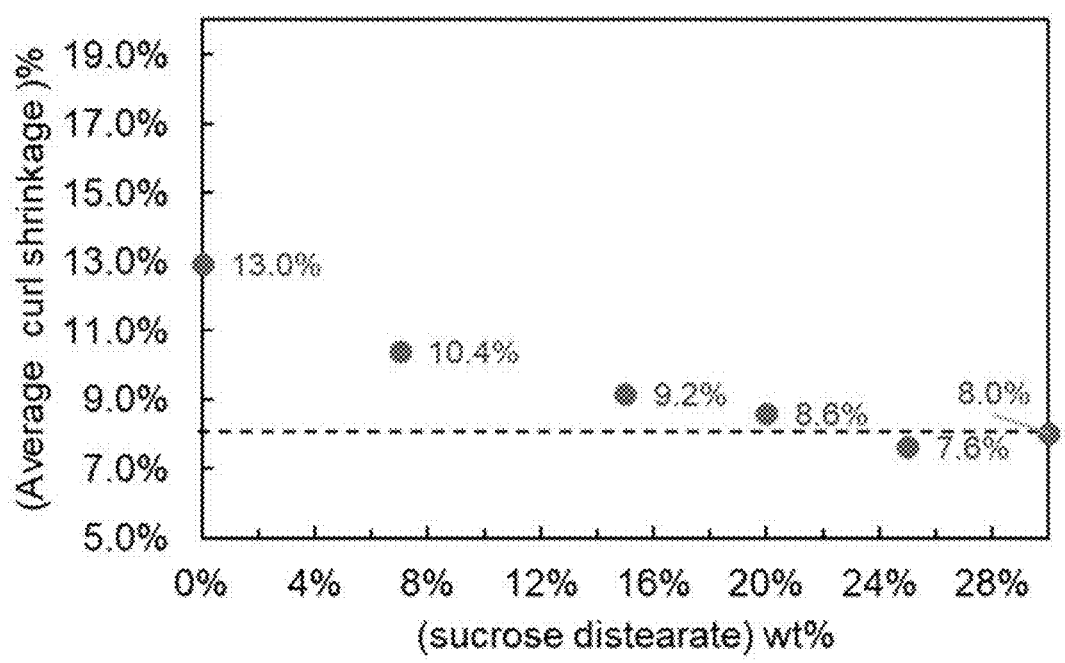
FIG. 2 is a graph showing average curl elongation achieved by treating hair with compositions in Table 2.

The length of each hair swatch was measured immediately (t=0), at about 14 hours (t=14), and at about 24 hours (t=24) after one of compositions 2A-2E and C3 was applied to the swatch. The elongation effect was evaluated by measuring the change in length of the swatches after application of the testing solutions. The result is illustrated in FIG. 2, which shows the average curl shrinkage for three swatches of each of compositions 2A-2E and C3.

This Example demonstrates that long-lasting beneficial effects of elongation of curls is achieved at all tested concentrations of sucrose ester, relative to the comparative composition without any sucrose ester.

It will be apparent to those skilled in the art that various modifications and variations can be made in the compositions and methods according to the disclosure without departing from the spirit or scope of the disclosure. Thus, it is intended that the disclosure cover such modifications and variations and their equivalents.

The invention claimed is:

1. A method for styling hair comprising applying to the hair a leave-in hair styling composition comprising:
    (a) at least one sucrose ester;
    (b) at least one nonionic polysaccharide thickening agent;
    (c) at least one cationic surfactant; and
    (d) at least one emulsifier chosen from fatty alcohols, esters, or a combination thereof,
    wherein the at least one sucrose ester is chosen from sucrose stearate, sucrose distearate, sucrose tristearate, sucrose polystearate, sucrose cocoate, sucrose laurate, sucrose palmitate, sucrose dipalmitate, or combinations thereof,
    wherein the at least one sucrose ester is present in an amount of at least 6% by weight, relative to the total weight of the composition, and
    wherein the method for styling hair is a method for elongating hair curls, providing hair curl definition, and/or providing hair curl hold, and leaving the hair styling composition in the hair for at least 30 minutes to style the hair.

2. The method of claim 1, wherein the hair styling composition further comprises at least one additional component chosen from (e) at least one $C_3$-$C_8$ polyol chosen from diols, triols, or a combination thereof, (f) at least one fatty compound, or combinations thereof.

3. The method of claim 1, wherein the hair styling composition comprises:
    (a) from 6% to about 20%, by weight, of the at least one sucrose ester;
    (b) from about 0.1% to about 5%, by weight, of the at least one nonionic polysaccharide thickening agent;
    (c) from about 0.1% to about 10%, by weight, of the at least one cationic surfactant;
    (d) from about 0.5% to about 10%, by weight, of the at least one emulsifier chosen from fatty alcohols, esters, or combinations thereof;
    (e) optionally, from about 3% to about 15%, by weight, of at least one $C_3$-$C_8$ polyol chosen from diols, triols, or a combination thereof; and
    (f) optionally, from about 1% to about 10%, by weight, of at least one fatty compound.

4. The method of claim 1, wherein the at least one nonionic polysaccharide thickening agent is chosen from gums, celluloses, starches, or combinations thereof.

5. The method of claim 1, wherein the at least one nonionic polysaccharide thickening agent is present in an amount ranging from about 0.01% to about 10% by weight, relative to the total weight of the composition.

6. The method of claim 1, wherein the at least one cationic surfactant is chosen from amidoamines, monoalkyl quaternary amines, dialkyl quaternary amines, polyquaternium compounds, salts thereof, or combinations thereof.

7. The method of claim 1, wherein the at least one cationic surfactant is present in an amount ranging from about 0.1% to about 15% by weight, relative to the total weight of the composition.

8. The method of claim 1, wherein the at least one emulsifier chosen from fatty alcohols, esters, or combinations thereof is present in an amount ranging from about 0.01% to about 15% by weight, relative to the total weight of the composition.

9. The method of claim 2, wherein the at least one $C_3$-$C_8$ polyol chosen from diols, triols, or a combination thereof is present in the composition in amount ranging from about 3% to about 20% by weight, relative to the total weight of the composition.

10. The method of claim 2, wherein the at least one fatty compound is present in the composition in amount ranging from about 0.01% to about 15% by weight, relative to the total weight of the composition.

11. The method of claim 1, wherein the hair styling composition is applied to wet hair.

12. The method of claim 1, wherein the hair styling composition further comprises at least one additional component chosen from (e) from about 3% to about 15%, by weight, of at least one $C_3$-$C_8$ polyol chosen from diols, triols, or a combination thereof, (f) from about 1% to about 10%, by weight, of at least one fatty compound, or combinations thereof.

13. A kit comprising a container comprising the hair styling composition according to claim 1.

14. The kit of claim 13, wherein the hair styling composition further comprises at least one additional component chosen from (e) at least one $C_3$-$C_8$ polyol chosen from diols, triols, or a combination thereof, (f) at least one fatty compound, or combinations thereof.

15. A method for styling curly hair by elongating hair curls, the method comprising:
 i. applying to wet hair a leave-in hair styling composition in an amount effective to elongate the hair curls, comprising:
  (a) from about 6% to about 20%, by weight, of at least one sucrose ester chosen from sucrose stearate, sucrose distearate, sucrose tristearate, sucrose polystearate, sucrose cocoate, sucrose laurate, sucrose palmitate, sucrose dipalmitate, or combinations thereof;
  (b) at least one nonionic polysaccharide thickening agent;
  (c) at least one cationic surfactant; and
  (d) at least one emulsifier chosen from fatty alcohols, esters, or a combination thereof, and
 ii. drying the wet hair without rinsing the leave-in hair styling composition from the hair, wherein the steps (i) and (ii) are performed sequentially in order to style the hair.

16. The method according to claim 15, wherein the hair styling composition further comprises at least one additional component chosen from (e) at least one $C_3$-$C_8$ polyol chosen from diols, triols, or a combination thereof, (f) at least one fatty compound, or combinations thereof.

17. The method according to claim 15, wherein the hair styling composition comprises from about 0.1% to about 5%, by weight, of the at least one nonionic polysaccharide thickening agent chosen from gums, celluloses, starches, or combinations thereof.

18. The method according to claim 15, wherein the hair styling composition comprises from about 0.1% to about 10%, by weight, of the at least one cationic surfactant chosen from amidoamines, monoalkyl quaternary amines, dialkyl quaternary amines, polyquaternium compounds, salts thereof, or combinations thereof.

19. The method according to claim 15, wherein the hair styling composition comprises from about 0.5% to about 10%, by weight, of the at least one emulsifier chosen from fatty alcohols, esters, or combinations thereof.

20. The method according to claim 15, wherein the hair styling composition comprises:
 (a) from 6% to about 20% of the at least one sucrose ester;
 (b) from about 1% to about 2%, by weight, of the at least one nonionic polysaccharide thickening agent;
 (c) from about 1% to about 3%, by weight, of the at least one cationic surfactant;
 (d) from about 2% to about 5%, by weight, of the at least one emulsifier chosen from fatty alcohols, esters, or combinations thereof; and
 (e) at least one $C_3$-$C_8$ polyol chosen from diols, triols, or a combination thereof.

* * * * *